(12) United States Patent
Kishima et al.

(10) Patent No.: US 8,759,790 B2
(45) Date of Patent: *Jun. 24, 2014

(54) FLUORESCENCE IMAGE PRODUCING METHOD, FLUORESCENCE IMAGE PRODUCING APPARATUS, AND FLUORESCENCE IMAGE PRODUCING PROGRAM

(71) Applicant: Sony Corporation, Tokyo (JP)

(72) Inventors: Koichiro Kishima, Kanagawa (JP); Takashi Yamamoto, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,492

(22) Filed: Apr. 2, 2013

(65) Prior Publication Data

US 2013/0221240 A1 Aug. 29, 2013

Related U.S. Application Data

(63) Continuation of application No. 12/851,748, filed on Aug. 6, 2010, now Pat. No. 8,421,033.

(30) Foreign Application Priority Data

Aug. 31, 2009 (JP) ................................. 2009-200890

(51) Int. Cl.
*G01N 21/64* (2006.01)
(52) U.S. Cl.
CPC .................................. *G01N 24/6458* (2013.01)
USPC ....................................................... 250/458.1

(58) Field of Classification Search
CPC ................................................. G01N 21/6458
USPC ........................................... 250/458.1, 459.1
See application file for complete search history.

(56) References Cited

U.S. PATENT DOCUMENTS

| | | | |
|---|---|---|---|
| 6,674,574 B1 | 1/2004 | Aono | |
| 7,232,980 B2 | 6/2007 | Oshiro et al. | |
| 7,272,252 B2 | 9/2007 | De La Torre-Bueno et al. | |
| 7,304,790 B2 | 12/2007 | Kawano et al. | |
| 7,564,621 B2 | 7/2009 | Kawano et al. | |
| 8,421,033 B2* | 4/2013 | Kishima et al. | 250/458.1 |
| 8,450,703 B2* | 5/2013 | De Boer et al. | 250/459.1 |
| 2003/0184856 A1 | 10/2003 | Otaki | |
| 2005/0056767 A1 | 3/2005 | Kaplan et al. | |

FOREIGN PATENT DOCUMENTS

| | | |
|---|---|---|
| DE | 19630322 | 1/1997 |
| JP | 2001-091822 | 4/2001 |
| JP | 2003-222801 | 8/2003 |
| JP | 2004-004634 | 1/2004 |

(Continued)

OTHER PUBLICATIONS

EP Search Report for corresponding 10008255.1 dated Mar. 30, 2011; 5 pages.

*Primary Examiner* — Constantine Hannaher
(74) *Attorney, Agent, or Firm* — K&L Gates LLP

(57) ABSTRACT

Method and apparatus for producing an image associated with a biological sample is disclosed. A processor focuses on a portion of the biological sample based on fluorescence of a first fluorescent material and captures an image of the portion of the biological sample based on fluorescence of the first fluorescent material and the second fluorescent material.

31 Claims, 11 Drawing Sheets

(56) References Cited

FOREIGN PATENT DOCUMENTS

| | | |
|---|---|---|
| JP | 2004-538509 | 12/2004 |
| JP | 2005-062515 | 3/2005 |
| JP | 2005-140956 | 6/2005 |
| JP | 2005-275156 | 10/2005 |
| JP | 2005-284136 | 10/2005 |
| JP | 2005-316383 | 11/2005 |
| JP | 2006-030304 | 2/2006 |
| JP | 2006-058642 | 3/2006 |
| WO | 2005-114293 | 12/2005 |
| WO | 2007070382 | 6/2007 |
| WO | 2009016548 | 2/2009 |

* cited by examiner

FLUORESCENCE IMAGE PRODUCING METHOD, FLUORESCENCE IMAGE PRODUCING APPARATUS, AND FLUORESCENCE IMAGE PRODUCING PROGRAM

CROSS REFERENCES TO RELATED APPLICATIONS

The present application is a continuation of U.S. application Ser. No. 12/851,748, filed on Aug. 6, 2010, which claims priority to Japanese Priority Patent Application JP 2009-200890 filed in the Japan Patent Office on Aug. 31, 2009, the entire content of which is hereby incorporated by reference.

BACKGROUND

The present application relates to a fluorescence image producing method, a fluorescence image producing apparatus, and a fluorescence image producing program that are suitable for a field of observing a tissue section, for example.

In general, a biological sample is fixed to a supporting base such as a glass slide and stained in a predetermined manner before being used in the field of pathology.

In a pathological diagnosis, the presence of a malignant tumor is primarily determined in a morphological view using a sample made by performing a Hematoxylin-Eosin (HE) staining on the tissue section or performing a Papanicolaou staining on the secretion cell. If a malignant tumor or a suspected site with the malignant tumor is found, the presence, the type, and the stage of the malignant tumor are secondarily determined in a molecular biological view using a sample made by performing a fluorescence staining on the tissue section or the secretion cell.

After a long storage period of such a sample, degradation of quality and discoloration of the biological sample occur and microscopic visibility of the biological sample also lowers, in general. Because the sample is sometimes diagnosed in a laboratory other than a facility where the sample is made such as a hospital, the biological sample is generally sent by mail, which takes a certain time.

In view of such situations, there is proposed an apparatus for storing the biological sample in the form of an image data (see, for example, Japanese Unexamined Patent Application No. 2003-222801).

By the way, in a case of obtaining an image of the entire biological sample enlarged to a predetermined scale, it is difficult to form the entire image on an imaging surface, and therefore a technique is generally used in which the biological sample is sectioned and enlargements of sectioned parts are connected together. Because this technique includes a step of moving a stage to focus on the sample with respect to each part of the sample, it takes a longer time to connect the enlargements of the parts.

SUMMARY

However, in a case of connecting the enlarged images of the sample parts where the fluorescence staining is performed, due to the longer time taken to connect the enlargements of the parts, not only the discoloration of fluorescent material to be labeled to a target is accelerated but also the biological sample is overloaded.

On the other hand, the sample performed with the fluorescence staining is not taken as an image because it is clear and colorless in an unexcited state, and therefore it is difficult to focus on the image based on the contrast of the image.

It is therefore desirable to provide the fluorescence image obtaining method, the fluorescence image obtaining apparatus, and the fluorescence image obtaining program that can focus on an image without accelerating the discoloration of the fluorescent material to be labeled to the target or overloading the biological sample.

In an embodiment, a method of producing an image associated with a biological sample is provided. The method includes focusing on the biological sample based on fluorescence of a first fluorescent material, wherein the biological sample is stained with the first fluorescent material and a second fluorescent material; and capturing the image based on fluorescence of the second fluorescent material, wherein the first and second fluorescent materials have different excitation wavelengths.

In an embodiment, the image is produced in a dark field imaging mode.

In an embodiment, the image is produced in a dark field imaging mode in combination with a bright field imaging mode.

In an embodiment, the image is captured as an entire image.

In an embodiment, the image is captured as a partial image.

In an embodiment, the image is captured as a plurality of partial images that are connected to form the image.

In an embodiment, image production is controlled by a data processing unit including control of focusing and capturing.

In an embodiment, after focusing, an excitation light source is driven by the data processing unit to initiate image capturing.

In an embodiment, a part of the biological sample is focused at a predetermined location.

In an embodiment, a part of the biological sample is focused at a variable location.

In another embodiment, an apparatus for producing an image associated with a biological sample is provided. The apparatus includes a base unit configured to receive the biological sample that is stained with a first fluorescent material and a second fluorescent material having different excitation wavelengths; a first light source configured to irradiate the biological sample thereby allowing focusing of the biological sample based on fluorescence of the first fluorescent material; and a second light source configured to irradiate the biological sample thereby allowing capturing of the image based on fluorescence of the second fluorescent material.

In an embodiment, the apparatus further includes a data processing unit configured to control image production including in communication with the base unit, the first light source and the second light source.

In an embodiment, the data processing unit stops driving the first light source and starts driving the second light source to initiate image capturing.

In a further embodiment, a computer readable memory device is provided storing instructions to cause a data processing unit to focus on a biological sample based on fluorescence of a first fluorescent material, wherein the biological sample is stained with the first fluorescent material and a second fluorescent material; and capture an image associated with the biological sample based on fluorescence of the second fluorescent material, wherein the first and second fluorescent materials have different excitation wavelengths.

In yet another embodiment, a method of producing an image associated with a biological sample is provided. The method includes irradiating the biological sample at a first excitation wavelength; focusing on the biological sample;

irradiating the biological sample at a second excitation wavelength; and capturing the image associated with the biological sample.

In yet a further embodiment, an apparatus for producing an image associated with a biological sample is provided. The apparatus includes a first light source configured to irradiate the biological sample at a first excitation wavelength thereby allowing focusing of the biological sample; and a second light source configured to irradiate the biological sample at a second excitation wavelength thereby allowing capturing of the image.

According to an embodiment, the sample part is irradiated with the excitation light for the fluorescent material to be labeled to the control for counterstain, which is contained more than the target, when a dark field image of a focusing object is obtained, and the sample part is irradiated with the excitation light for the fluorescent material to be labeled to the target when a dark field image of a recording object is obtained.

Therefore, the focus can be adjusted using the image of the sample part of the fluorescent material to be labeled to the control for counterstain, which is contained more than the target, without making the fluorescent material to be labeled to the target emit a light. As a result, the focus can be adjusted without accelerating the discoloration of the fluorescent material to be labeled to the target or overloading the biological sample.

Additional features and advantages are described herein, and will be apparent from the following Detailed Description and the figures.

DETAILED DESCRIPTION

The present application will be explained below in greater detail with reference to the drawings according to an embodiment.

<1. Embodiment>
[1-1. Configuration of biological sample image obtaining apparatus]
[1-2. Configuration of microscope]
[1-3. Configuration of data processing unit]
[1-4. Specific processing of bright field imaging mode]
[1-5. Specific processing of dark field imaging mode]
[1-6. Image obtaining process in dark field imaging mode]
[1-7. Effects]
<2. Other embodiments>

1. Embodiment 1-1. Configuration of Biological Sample Image Obtaining Apparatus

Figure 1:
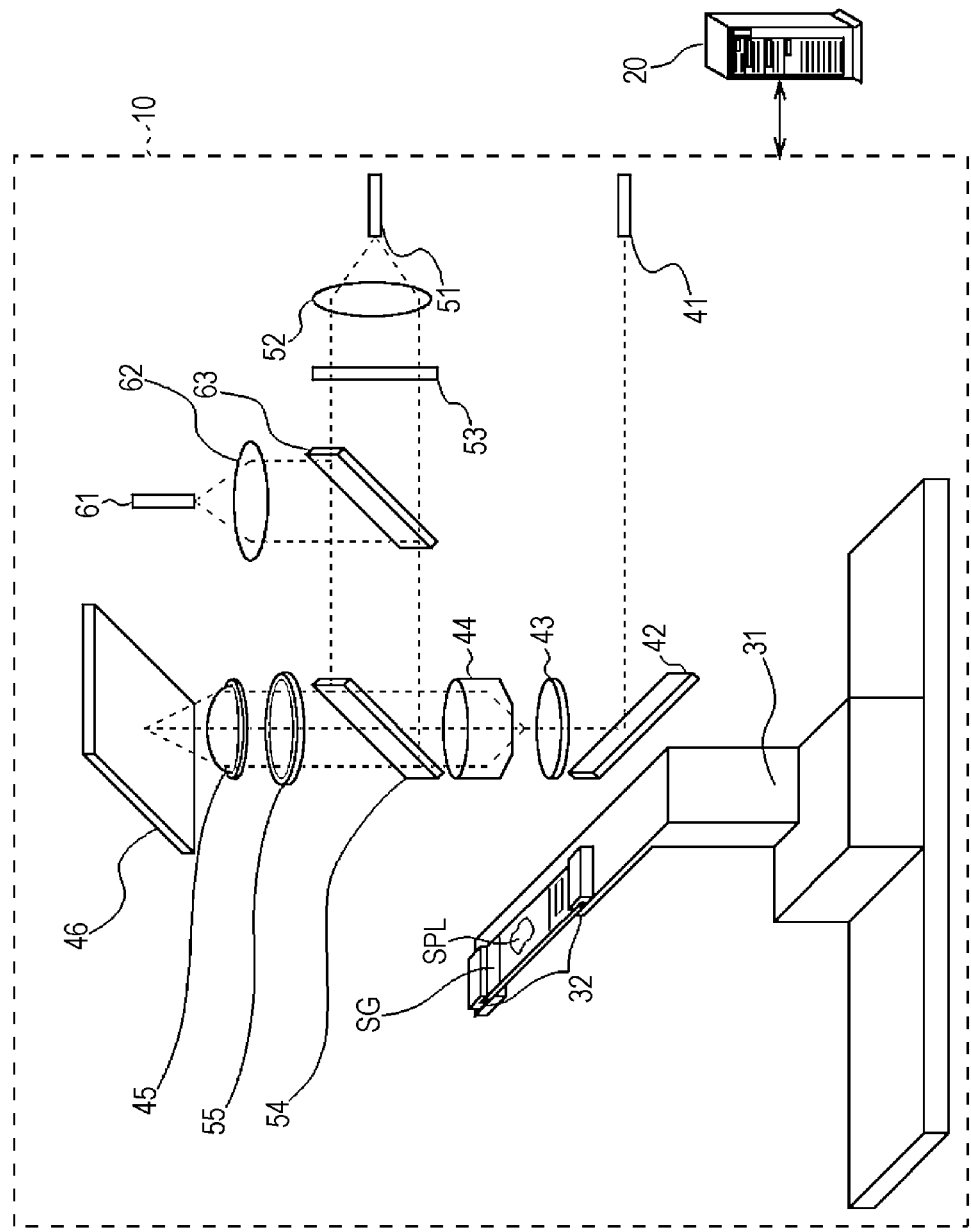
FIG. 1 schematically illustrates a configuration of a biological sample image obtaining apparatus.

FIG. 1 illustrates a biological sample image obtaining apparatus 1 according to an embodiment. The biological sample image obtaining apparatus 1 includes a microscope 10 and a data processing unit 20.

1-2. Configuration of Microscope

The microscope 10 includes a stage (also referred to below as a movable stage) 31 movable in all directions (x-axis, y-axis, and z-axis directions) parallel to and perpendicular to a plane on which a slide SG such as a glass plate is placed (also referred to below as a slide placement plane). A slide holder 32 is provided on the slide placement plane.

When the slide SG is set, the slide holder 32 is moved to a position specified as a setting place (also referred to below as a slide setting position). At the slide setting position, the slide SG contained in a slide container (not shown) is removed and set in the slide holder 32 by a slide setting mechanism (not shown).

A tissue section or a secretion cell including a connective tissue such as blood, an epithelial tissue, or both of them is fixed to the slide SG contained in the slide container (not shown) as a biological sample SPL by a predetermined fixation technique, and stained as necessary.

The staining includes not only typical staining techniques represented by a Hematoxylin-Eosin (HE) staining, a Giemsa staining, and a Papanicolaou staining but also fluorescence staining techniques represented by a fluorescence in situ hybridization (FISH) and an enzyme antibody technique.

In addition to a fluorescent label applied to a probe (also referred to below as a fluorescence marker), the fluorescence staining technique generally uses another fluorescent label to be contrasted with the fluorescence marker on the probe (also referred to below as a control marker).

The control marker has an excitation wavelength different from the excitation wavelength of the fluorescence marker. For example, the excitation wavelength may be approximately 365 nm, and 4',6-diamidino-2-pheylindole (DAPI) is commonly used. With the DAPI, a target to be contrasted with the target of the fluorescence marker (also referred to below as a control target) is a cell nucleus.

When an image of the biological sample SPL is taken, the slide holder 32 is moved to a position specified as a location for a microscopic examination (also referred to below as a microscopic position). In this case, either a bright field imaging mode or a dark field imaging mode is executed.

In the case of the bright field imaging mode, an illuminating light is emitted from a bright field light source 41 to the biological sample SPL. The illuminating light is reflected by a reflection mirror 42, irradiated onto the biological sample SPL in the microscopic position as a visible light through a bright field filter 43, and then reaches an objective lens 44.

The magnification power of the objective lens 44 is either as low as an image of the entire biological sample SPL (also referred to below as a bright field entire image) can be formed or as high as an image of only a part of the biological sample SPL (also referred to below as a bright field partial image) can be formed.

The microscope 10 forms an image of the biological sample SPL obtained through the illuminating light on an imaging surface of an imaging device 46 as the bright field entire image or the bright field partial image after enlarging the image using the objective lens 44 and an imaging lens 45.

As described above, the microscope 10 is configured to obtain an entire or partial bright field image (the bright field entire image or the bright field partial image) of the biological sample SPL in the bright field imaging mode.

In FIG. 1, there are a dichroic mirror 54 and an emission filter 55 on a light path between the objective lens 44 and the imaging lens 45. However, in the case of the bright field imaging mode, the dichroic mirror 54 and the emission filter 55 are retired from the light path so that the visible light entering through the bright field filter 43 is not absorbed or reflected by the mirror and the filter.

On the other hand, in the case of the dark field imaging mode, a light that excites both the fluorescence marker on the probe and the control marker (also referred to below as an excitation light) is emitted from an excitation light source 51. The magnification power of the objective lens 44 when the excitation light is emitted is as high as a part of a fluorescence image of the biological sample SPL (also referred to below as a dark field partial image) can be formed.

A collimator lens 52 makes the excitation light emitted from the excitation light source 51 into a parallel beam, and an excitation filter 53 eliminates lights other than the excitation light. The excitation light transmitted through the excitation filter 53 is reflected by the dichroic mirror 54, and then focused on the microscopic position by the objective lens 44.

When the probe is coupled to the target and the control target of the biological sample SPL in the microscopic position, the fluorescence marker applied to the probe and the control marker produce a luminescence by the excitation light. The luminescence is transmitted through the dichroic mirror 54 via the objective lens 44 and reaches the imaging lens 45 after the lights other than the luminescence of the fluorescent material are absorbed by the emission filter 55.

The microscope 10 enlarges an image obtained through the luminescence of the fluorescence marker and the control marker using the objective lens 44 and the imaging lens 45, and forms the enlarged image on the imaging surface of the imaging device 46 as the dark field partial image.

As described above, the microscope 10 is configured to obtain a fluorescence image of the sample part (dark field partial image) in the dark field imaging mode.

Although FIG. 1 shows a dichroic mirror 63 on the light path between the excitation filter 53 and the dichroic mirror 54, the dichroic mirror 63 transmits the excitation light that is transmitted through the excitation filter 53.

Figure 2:
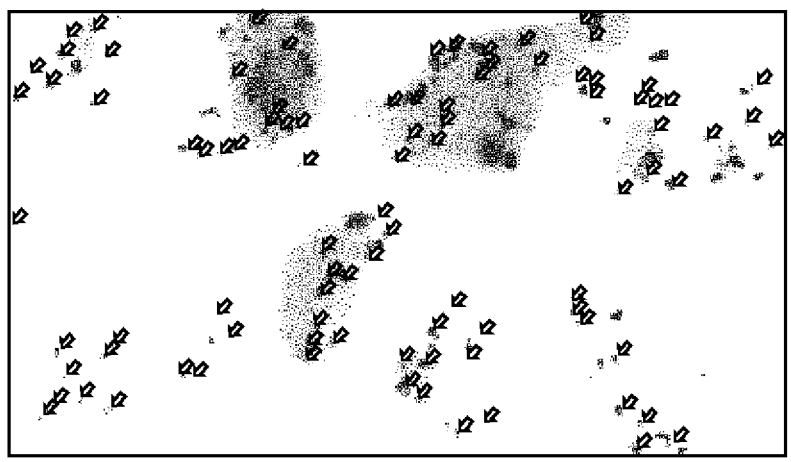
FIG. 2 schematically illustrates a fluorescence image.

FIG. 2 shows an example of the fluorescence image of the biological sample SPL (dark field partial image). The image shown in FIG. 2 is taken by staining a mammary tissue by the FISH technique using a reagent called PathVysion HER-2DNA probe kit produced by Abbott Laboratories.

Points indicated by arrows in FIG. 2 represent the fluorescence marker, specifically the fluorescence marker applied to the probes for the HER2/neu genes encoding the HER2 protein. Concentrated areas with shades in FIG. 2 represent the control marker forming an outer shape substantially matching the outer shape of the tissue with the HE stain.

Although the reagent includes the fluorescence marker of the probes for the alpha satellite DNA sequence in the centromere region of the seventeenth chromosome as well as the probes for the HER2/neu genes, the fluorescence marker is omitted in FIG. 2 for convenience.

In addition to the configuration described above, the microscope 10 includes a light source (also referred to below as a control-marker excitation light source) 61 configured to emit an excitation light that excites the control marker while leaving the fluorescence marker unexcited (also referred to below as a control-marker exclusive excitation light).

The control-marker exclusive excitation light is emitted from the control-marker excitation light source 61 in a focusing process when the dark field partial image of the biological sample SPL is obtained.

The control-marker exclusive excitation light emitted from the control-marker excitation light source 61 is made into a parallel beam by a collimator lens 62, reflected by the dichroic mirror 63 and the dichroic mirror 54, and then focused on the microscopic position by the objective lens 44.

When the probe is coupled to the control target of the biological sample SPL in the microscopic position, the control marker applied to the probe produces a luminescence by the control-marker exclusive excitation light. The luminescence is transmitted through the dichroic mirror 54 via the objective lens 44 and reaches the imaging lens 45 after the lights other than the luminescence of the fluorescent material are absorbed by the emission filter 55.

The microscope 10 enlarges an image obtained through the luminescence of the control marker using the objective lens 44 and the imaging lens 45, and forms the enlarged image on the imaging surface of the imaging device 46 as the dark field partial image.

The data processing unit 20 controls the movable stage 31 based on the dark field partial image so that the corresponding sample part is focused on. Furthermore, when the sample part is focused on, the data processing unit 20 makes the excitation light source 51 emit the excitation light instead of the control-marker excitation light source 61, and stores the dark field partial image obtained with the excitation light.

As described above, the biological sample image obtaining apparatus 1 is configured to obtain the dark field partial image obtained with the control-marker exclusive excitation light as the dark field partial image of the focusing object, and obtain the dark field partial image obtained with the excitation light as the dark field partial image of the recording object.

1-3. Configuration of Data Processing Unit

Figure 3:
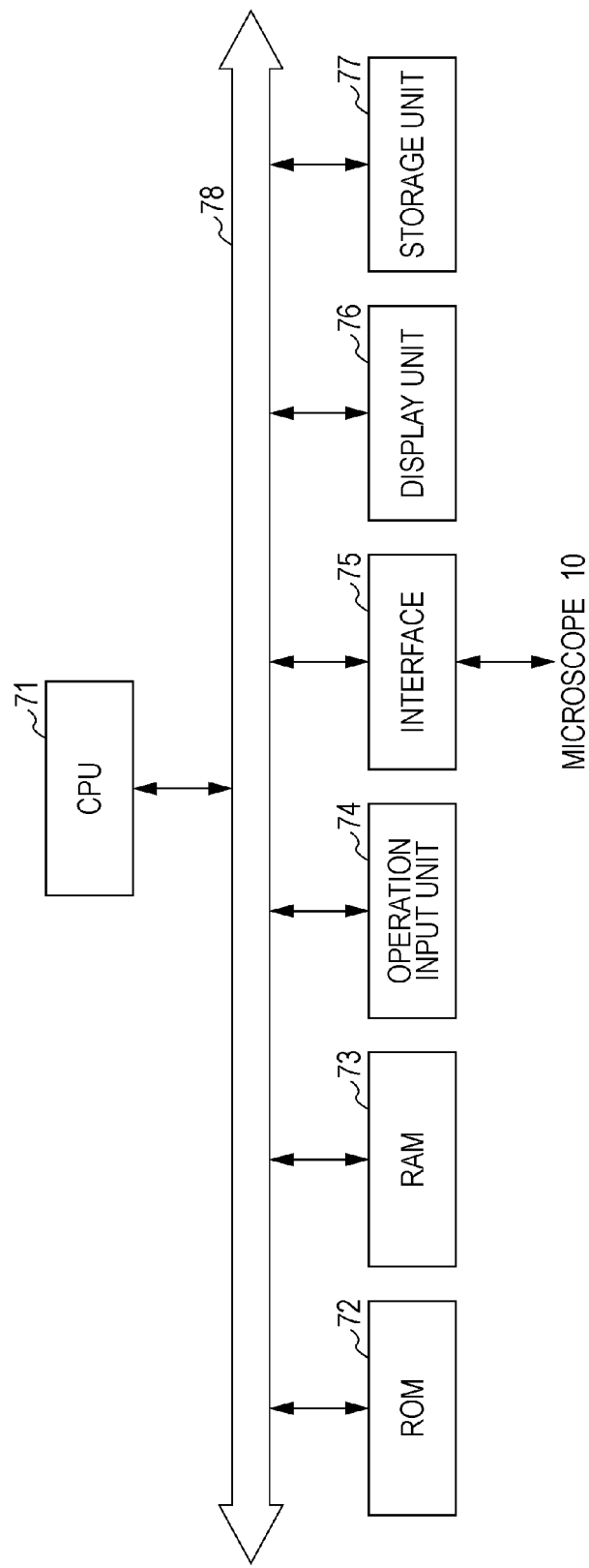
FIG. 3 is a block diagram showing a configuration of a data processing unit.

A configuration of the data processing unit 20 is explained below. As shown in FIG. 3, the data processing unit 20 includes a central processing unit (CPU) 71 that performs various controls and various types of hardware connected to the CPU 71.

Specifically, a read only memory (ROM) 72, a random access memory (RAM) 73 that serves as a working memory of the CPU 71, an operation input unit 74 that inputs a command corresponding to a user operation, an interface 75, a display unit 76, and a storage unit 77 are connected to the CPU 71 via a bus 78.

The ROM 72 stores computer programs for performing various processings. The interface 75 is connected to the microscope 10 (drive systems of the movable stage 31, the light sources 41, 51, 61, the imaging device 46, the objective lens 44, and the emission filter 55).

As the display unit 76, a liquid crystal display, an electroluminescence (EL) display, or a plasma display may be used. As the storage unit 77, a magnetic disk such as a hard disk (HD), a semiconductor memory, or an optical disk may be used. Alternatively, a portable memory such as a universal serial bus (USB) memory and a compact flash (CF) memory may be used.

The CPU 71 loads a computer program corresponding to the command provided by the operation input unit 74 from among a plurality of the computer programs stored in the ROM 72 to the RAM 73, and controls the display unit 76 and the storage unit 77 according to the loaded program.

The CPU 71 is also configured to control each unit of the microscope 10 via the interface 75 according to the loaded program.

1-4. Specific Processing of Bright Field Imaging Mode

When the CPU 71 receives an execution command of the bright field imaging mode from the operation input unit 24, the CPU 71 loads a computer program corresponding to the imaging mode to the RAM 23.

Figure 4:
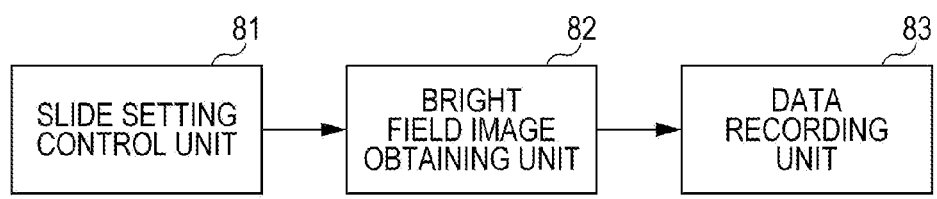
FIG. 4 is a block diagram showing a functional configuration of a central processing unit (CPU) that executes a bright field imaging mode.

In this case, according to the computer program corresponding to the bright field imaging mode, the CPU 71 functions as a slide setting control unit 81, a bright field image obtaining unit 82, and a data recording unit 83, as shown in FIG. 4.

The slide setting control unit 81 drives the movable stage 31 and positions the slide holder 32 in the slide setting position when the slide setting control unit 81 receives the execution command of the imaging mode or a notice that the bright field image obtaining unit 82 or the slide should be replaced.

In a case where the slide holder 32 is positioned in the slide setting position, the slide setting control unit 81 drives the movable stage 31 again after a predetermined waiting period to move the slide holder 32 from the slide setting position to the microscopic position. During the waiting period, as described with reference to FIG. 1, the slide SG contained in the slide container is set in the slide holder 32 by the slide setting mechanism.

For example, at the time point of the slide holder 32 being positioned in the microscopic position, the bright field image obtaining unit 82 arranges the objective lens 44 with low power on an optical axis between the dichroic mirror 54 and the imaging lens 45, and drives the bright field light source 41.

Figure 5:
FIG. 5 is a photograph showing a bright field entire image.

The bright field image obtaining unit 82 then focuses on the biological sample SPL based on the contrast of the bright field entire image formed by the imaging device 46, thereby obtaining, for example, the bright field entire image as shown in FIG. 5.

When the bright field entire image is obtained, bright field image obtaining unit 82 arranges a predetermined objective lens 44 with high power in a predetermined position on the light path instead of the objective lens 44 with low power arranged in the predetermined position on the light path.

The bright field image obtaining unit 82 then detects a contour of the biological sample SPL from the bright field entire image. Applied to the detection of the contour is, for example, a technique of performing a binarization process for distinguishing the biological sample SPL from other areas and then performing an extraction process of extracting the outer shape of the biological sample SPL.

Figure 6:
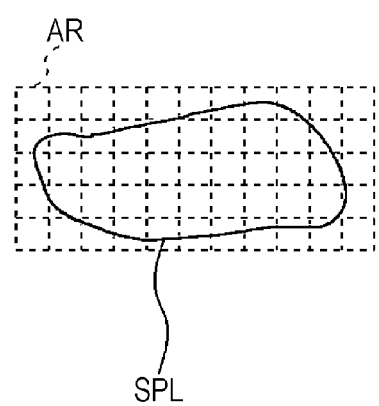
FIG. 6 is a schematic diagram for explaining an allocation of an imaging area of a biological sample.

Upon detecting the contour of the biological sample SPL from the bright field entire image, the bright field image obtaining unit 82 determines the size of an area in which the partial image should be taken (also referred to below as an imaging area), and allocates imaging areas AR to the biological sample SPL as shown in FIG. 6.

The imaging area AR is determined at least based on the magnification power of the objective lens 44 and the size of the imaging surface of the imaging device 46, and it is allocated under the condition of either including a part of the contour of the biological sample SPL or being included within the contour. Although the imaging areas AR do not overlap one another in FIG. 6, adjacent areas may partially overlap each other.

After allocating the imaging areas AR to the biological sample SPL in the bright field entire image, the bright field image obtaining unit 82 sequentially moves the movable stage 31 so that each part of the biological sample SPL becomes the imaging area AR, and obtains the bright field partial image of each part corresponding to the imaging area AR.

The bright field image obtaining unit 82 then connects the bright field partial images, thereby forming a connected image (also referred to below as a bright field part connected image). The bright field image obtaining unit 82 is configured to issue a notice to the slide setting control unit 81 at this time that the slide should be replaced.

When the bright field part connected image is formed by the bright field image obtaining unit 82, the data recording unit 83 generates data about the bright field partial images and the bright field entire image obtained in the process of generating the bright field part connected image as well as the bright field part connected image (also referred to below as bright field image data), and stores the data in the storage unit 77.

At this time, the data recording unit 83 generates data about the imaging areas AR allocated to the biological sample SPL in the bright field entire image by the bright field image obtaining unit 82 (also referred to below as imaging area allocation data), and associates the data with the bright field image data.

The data recording unit 83 is also configured to associate data about the biological sample SPL (also referred to below as sample data) with the bright field image data.

The sample data includes, for example, information such as the name, sexuality, and age of a subject of the examination, date of collecting the biological sample SPL, and the like. Also additional information can be obtained through an input from the operation input unit 74 or by a read unit that scans a bar-code on the glass slide SG.

1-5. Specific Processing of Dark Field Imaging Mode

When the CPU 71 receives an execution command of the dark field imaging mode from the operation input unit 24, the CPU 71 loads a computer program corresponding to the imaging mode to the RAM 23.

Figure 7:
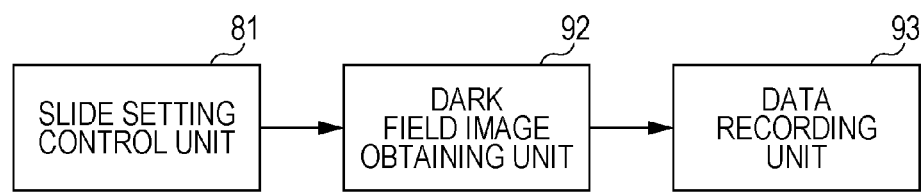
FIG. 7 is a block diagram showing a functional configuration of the CPU that executes a dark field imaging mode.

In this case, according to the computer program corresponding to the dark field imaging mode, the CPU 71 functions as the slide setting control unit 81, a dark field image obtaining unit 92, and a data recording unit 93, as shown in FIG. 7 in which the same reference numeral is applied to the same constituent shown in FIG. 4.

For example, at the time point of the slide holder 32 being positioned in the microscopic position, the dark field image obtaining unit 92 arranges the objective lens 44 with high power on the optical axis between the dichroic mirror 54 and the imaging lens 45.

At this time, the dark field image obtaining unit 92 also obtains the sample data about the biological sample SPL provided to the slide holder 32, and searches in the storage unit 77 for the sample data including, for example, the name of the subject and the date of collection matching those in the obtained sample data.

In a case where the sample data is not found in the storage unit 77, the dark field image obtaining unit 92 issues a notice of the fact through, for example, the display unit 76.

On the other hand, when the sample data is found in the storage unit 77, the dark field image obtaining unit 92 reads the imaging area allocation data associated with the sample data from the storage unit 77. The dark field image obtaining unit 92 then allocates the imaging areas AR (FIG. 6) to the biological sample SPL provided to the slide holder 32 at this time point in the same state as the allocation to the biological sample SPL in the bright field imaging mode.

Thus, only the part corresponding to the biological sample SPL on the glass slide SG fixed to the slide holder 32 is precisely allocated as an allocation object even when the fluorescent material in the biological sample SPL is not excited.

After allocating the imaging areas AR to the biological sample SPL, the dark field image obtaining unit 92 selects each sample part allocated with the imaging area AR as an imaging object in a predetermined order, and obtains an image (dark field partial image) of the sample part selected as the imaging object.

The way of obtaining the image (dark field partial image) of a single sample part selected as the imaging object is specifically explained below. That is, after moving the movable stage 31 in the x-axis direction or the y-axis direction so that the sample part of the biological sample SPL to be imaged is included in the imaging area, the dark field image obtaining unit 92 drives the control-marker excitation light source 61 to irradiate the biological sample SPL with the control-marker exclusive excitation light.

Figure 8:
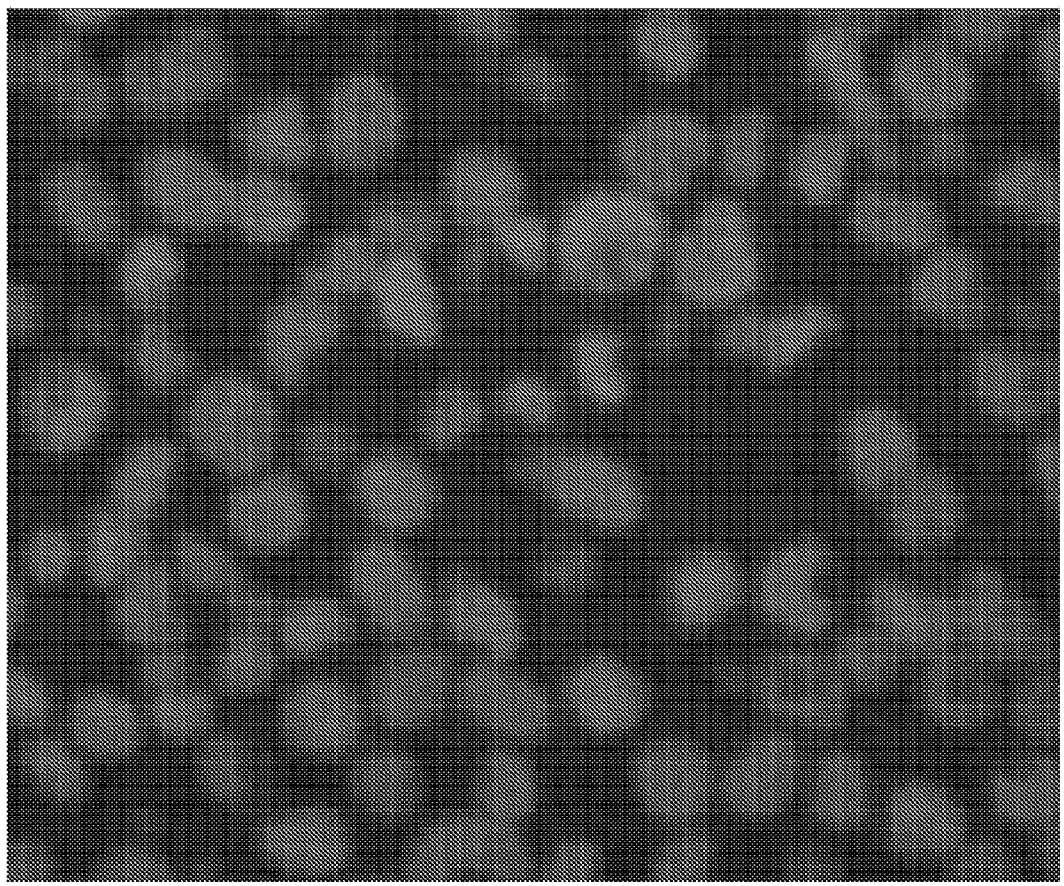
FIG. 8 is a photograph showing a dark field partial image of a control marker.

As a result, the imaging device 46 forms a dark field image (dark field partial image) of the control marker in the sample part to be imaged from among the control marker excited by the control-marker exclusive excitation light. FIG. 8 shows an example of the dark field partial image of the control marker.

The dark field image obtaining unit 92 obtains a part of the dark field partial image from the imaging device 46, and focuses on the sample part of the imaging object based on the contrast of the part. Accordingly, the focusing time is reduced compared with the case of focusing based on the contrast of the entire dark field partial image.

Figure 9A:
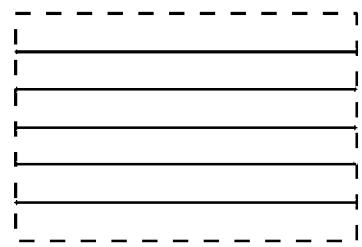
FIGS. 9A and 9B are schematic diagrams showing examples of an image to be used as a focusing object.
Figure 9B:
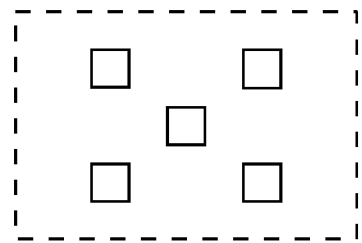

The part of the dark field partial image used as the focusing object may be, for example, defined by lines at a predetermined interval as shown in FIG. 9A, or defined as a group of a center pixel and pixels surrounding the center pixel as shown in FIG. 9B.

Figure 10:
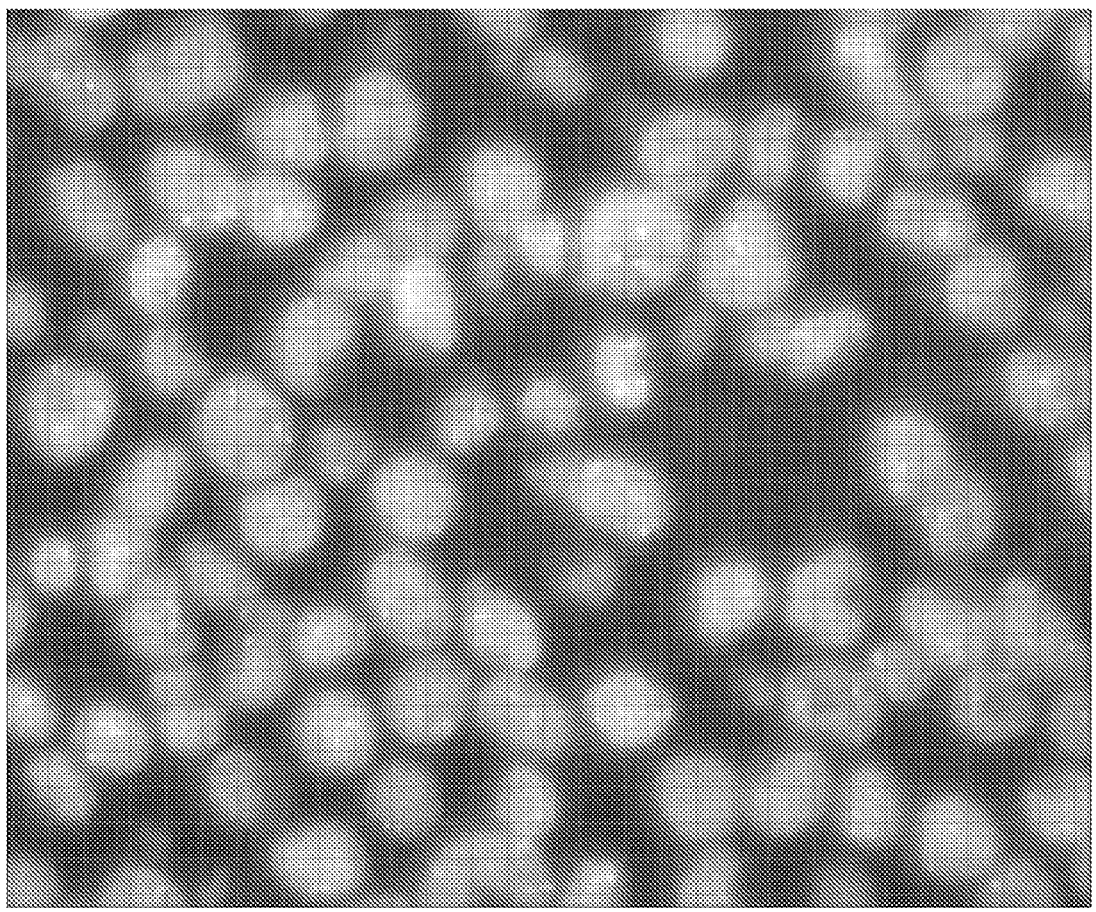
FIG. 10 is a photograph showing a dark field partial image of a control marker and the fluorescence marker.

Upon completion of focusing on the sample part of the imaging object, the dark field image obtaining unit 92 stops driving the control-marker excitation light source 61 and starts driving the excitation light source 51. As a result, the imaging device 46 forms a dark field image (dark field partial image) of the control marker and the fluorescence marker in the sample part of the imaging object as shown in FIG. 10, for example, among the whole control marker excited by the control-marker excitation light and the whole fluorescence marker.

The dark field image obtaining unit 92 obtains the entire dark field partial image from the imaging device 46 as the dark field partial image of the recording object.

As described above, the dark field image obtaining unit 92 obtains the dark field partial image of each sample part of the recording object in a predetermined order using the above-described obtaining technique.

When the dark field partial images of all the sample parts of the recording object are obtained, the dark field image obtaining unit 92 generates a connected image (also referred to below as a dark field part connected image) by connecting the dark field partial images to one another. At this time, the dark field image obtaining unit 92 notifies the slide setting control unit 81 that the slide should be replaced.

When the dark field partial images of all the sample parts of the recording object are obtained by the dark field image obtaining unit 92, the data recording unit 93 generates data about the dark field partial images and the dark field part connected image obtained in the process of generating the images (also referred to below as the dark field image data).

The data recording unit 93 then stores the dark field image data in the storage unit 77 in association with the bright field image data associated with the imaging area allocation data read by the dark field image obtaining unit 92 in the process of generating the dark field image data.

1-6. Image Obtaining Process in Dark Field Imaging Mode

Figure 11:
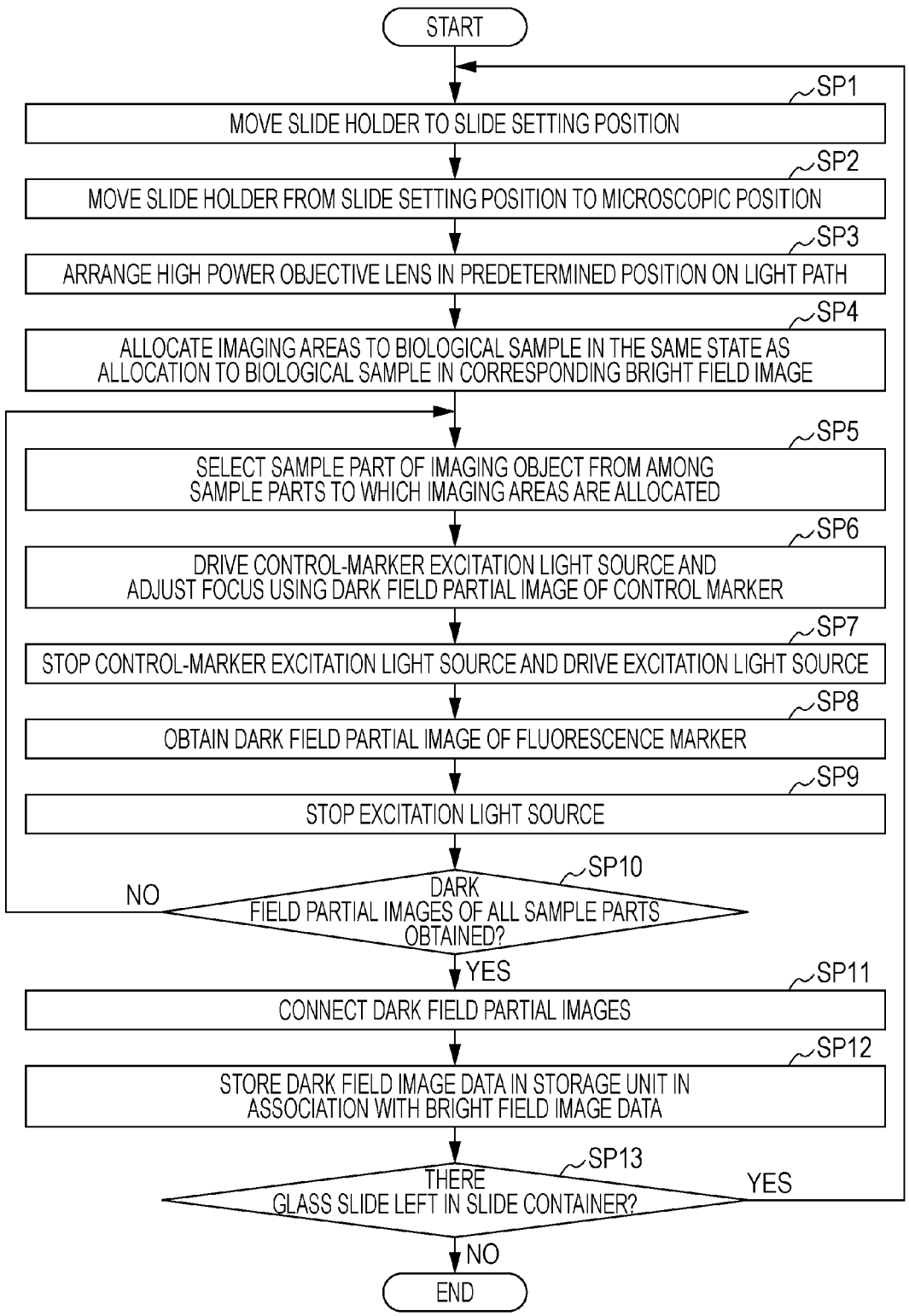
FIG. 11 is a flowchart showing a dark field image obtaining process.

A dark field image obtaining process is explained below with reference to a flowchart shown in FIG. 11.

Upon receipt of the execution command of the imaging mode, the CPU 71 starts the dark field image obtaining process, moves to Step SP1, positions the slide holder 32 in the slide setting position, and then moves to Step SP2.

At Step SP2, after the predetermined waiting period, the CPU 71 positions the slide holder 32 in the microscopic position from the slide setting position, and moves to Step SP3. At Step SP3, the CPU 71 arranges the objective lens 44 with high power on the optical axis between the dichroic mirror 54 and the imaging lens 45, and moves to Step SP4.

At Step SP4, the CPU 71 allocates the imaging areas AR (FIG. 6) to the biological sample SPL provided to the slide holder 32 in the same state as the allocation to the biological sample SPL in the bright field imaging mode, and moves to Step SP5.

At Step SP5, the CPU 71 selects one of the sample parts, as the imaging object, to which the imaging areas AR are allocated, and moves to Step SP6. At Step SP6, the CPU 71 drives the control-marker excitation light source 61, focuses on the sample part of the imaging object based on the contrast of a part of the dark field image (dark field partial image) of the control marker in the sample part of the imaging object, and moves to Step SP7.

At Step SP7, the CPU 71 stops driving the control-marker excitation light source 61 and starts driving the excitation light source 51 at the same time, and then moves to Step SP8. At Step SP8, the CPU 71 obtains the dark field image of the control marker and the fluorescence marker in the sample part of the imaging object as the dark field partial image of the recording object, and moves to Step SP9.

At Step SP9, the CPU 71 stops driving the excitation light source 51, and moves to Step SP10. At Step SP10, the CPU 71 determines whether the dark field partial images of all the sample parts allocated with the imaging areas AR are obtained, and returns to Step SP5 when there remains any sample part of which the dark field partial image is not obtained.

On the other hand, when the dark field partial images of all the sample parts are obtained, the CPU 71 moves to Step SP11, generates the dark field part connected image by connecting the dark field partial images, and moves to Step SP12.

At Step SP12, the CPU 71 generates the dark field image data about the dark field part connected image obtained at Step SP11 and the dark field partial images before being connected, stores the dark field image data in the storage unit 77 in association with the corresponding bright field image data, and moves to Step SP13.

At Step SP13, the CPU 71 determines whether there is any glass slide SG left in the slide container, and if there is any left, the CPU 71 returns to Step SP1 to repeat the process described above. On the other hand, if there is no glass slide SG left in the slide container, the CPU 71 terminates the dark field image obtaining process.

1-7. Effects

With the configuration described above, in a case of obtaining the dark field partial image, the biological sample image obtaining apparatus 1 drives the control-marker excitation light source 61 to irradiate the sample part of the imaging object with the control-marker exclusive excitation light. The biological sample image obtaining apparatus 1 then focuses on the part of the biological sample based on the contrast in the dark field image of the control marker in the sample part excited by the control-marker exclusive excitation light.

Upon completion of focusing on the sample part of the imaging object, the biological sample image obtaining apparatus 1 drives the excitation light source 51 instead of the control-marker excitation light source 61 to irradiate the sample part of the imaging object with the excitation light. The biological sample image obtaining apparatus 1 then obtains the dark field image of the fluorescence marker and the control marker in the sample part excited by the excitation light as the dark field partial image to be recorded.

Because the control marker targets a cell nucleus, its amount included in the biological sample SPL is much larger than that of the fluorescence marker that targets a certain gene, and the control marker produces a light vaguely presenting the biological sample as a whole.

Therefore, the biological sample image obtaining apparatus 1 can focus on each sample part of the biological sample SPL with a high accuracy without making the fluorescence marker emit a light and, as a result, obtain the dark field partial image of each sample part to be recorded.

By the way, as the excitation light source 51, a mercury lamp, a xenon lamp, or a metal halide lamp is used in general. Partially because the wavelength spectra of these lamps are stable, the transmittances of the excitation filer 53 and the emission filter 55 are adjusted so that the fluorescence marker appears brighter than the control marker.

Therefore, to observe the control marker using the excitation light source 51, the irradiation intensity of the excitation light source 51 is made higher compared with the case of observing the fluorescence marker. As a result, in this case, discoloration of both the fluorescence marker and the control marker is accelerated and also the biological sample SPL is overloaded.

On the other hand, to extract only a light that excites the control marker alone from the excitation light emitted from the excitation light source 51 using a filter, the filter is replaced when the dark field partial image is focused on and when dark field partial image is obtained. As a result, in this case, the size of the apparatus increases due to the increased number of the filters. Furthermore, it takes a longer time to obtain the dark field partial image in this case, and therefore this approach is not realistic.

On the contrary, the biological sample image obtaining apparatus 1 emits the control-marker exclusive excitation light from the control-marker excitation light source 61. Therefore, the biological sample image obtaining apparatus 1 can obtain the dark field partial image faster than the case of observing the control marker using the excitation light source 51 without accelerating the discoloration of both the fluorescence marker and the control marker.

With the configuration described above, the biological sample image obtaining apparatus 1 can adjust the focus without accelerating the discoloration of the fluorescent material to be labeled to the target or overloading the biological sample by using the dark field image of the control marker excited by the control-marker exclusive excitation light.

2. Other Embodiments

In the embodiment described above, a sample surface of the biological sample SPL facing the objective lens 44 is irradiated with the control-marker exclusive excitation light. However, a sample surface on the opposite side of the sample surface facing the objective 44 may be irradiated with the control-marker exclusive excitation light.

Figure 12:
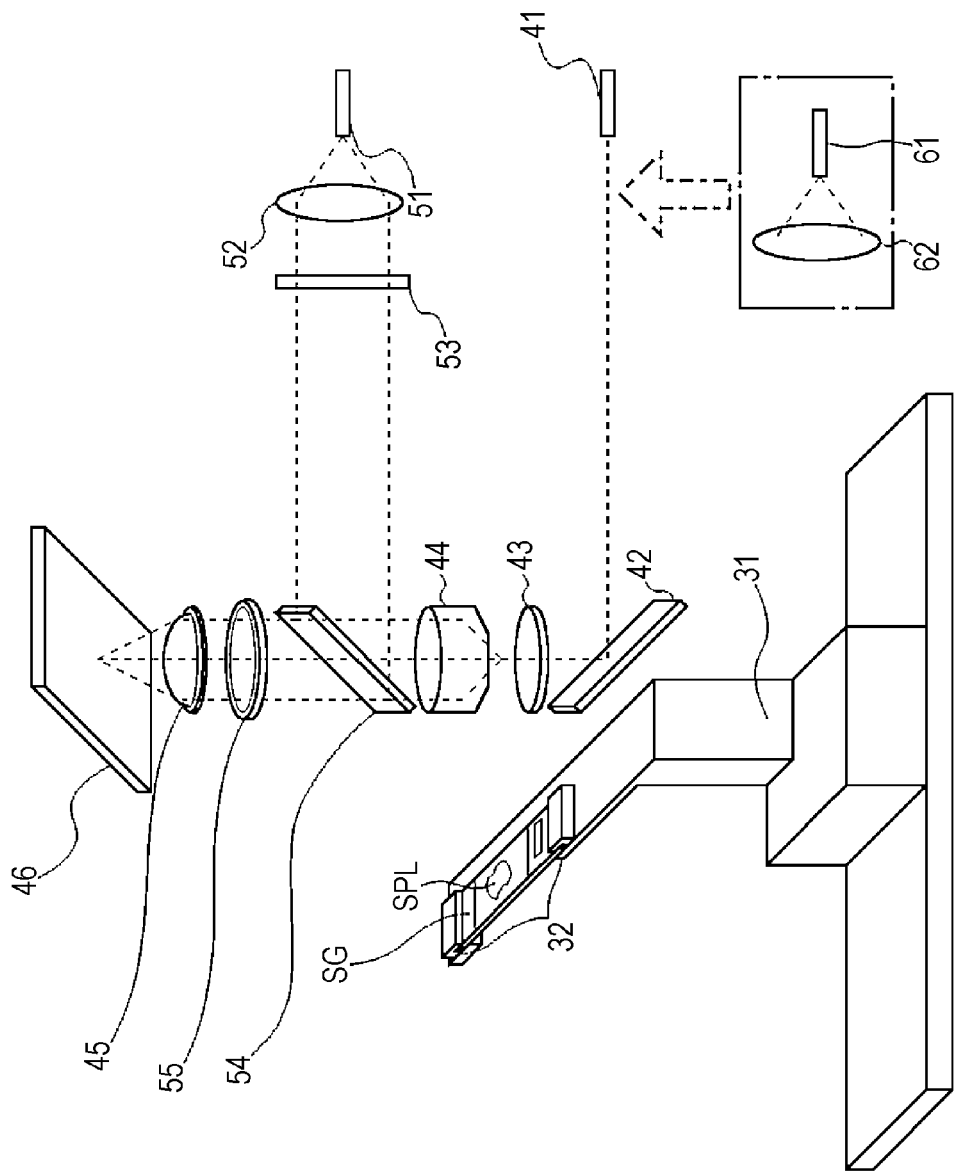
FIG. 12 schematically illustrates an arrangement of a control-marker excitation light source according to another embodiment.

FIG. 12 illustrates an example with the same reference numerals and symbols applied to the constituents corresponding to those in FIG. 1. In the example shown in FIG. 12, in the case of the dark field imaging mode, the control-marker excitation light source 61 is arranged in a predetermined light source position, where the bright field light source 41 is generally arranged, instead of the bright field light source 41. Furthermore, the collimator lens 62 is arranged on the light path between the light source and the reflection mirror 42, and the bright field filter 43 is removed from the light path. The control-marker exclusive excitation light emitted from the control-marker excitation light source 61 is made into a parallel beam by the collimator lens 62, and conducted to the sample surface on the opposite side of the sample surface facing the objective lens 44 via the reflection mirror 42. In the example shown in FIG. 12, the dichroic mirror 63 shown in FIG. 1 is omitted.

Figure 13:
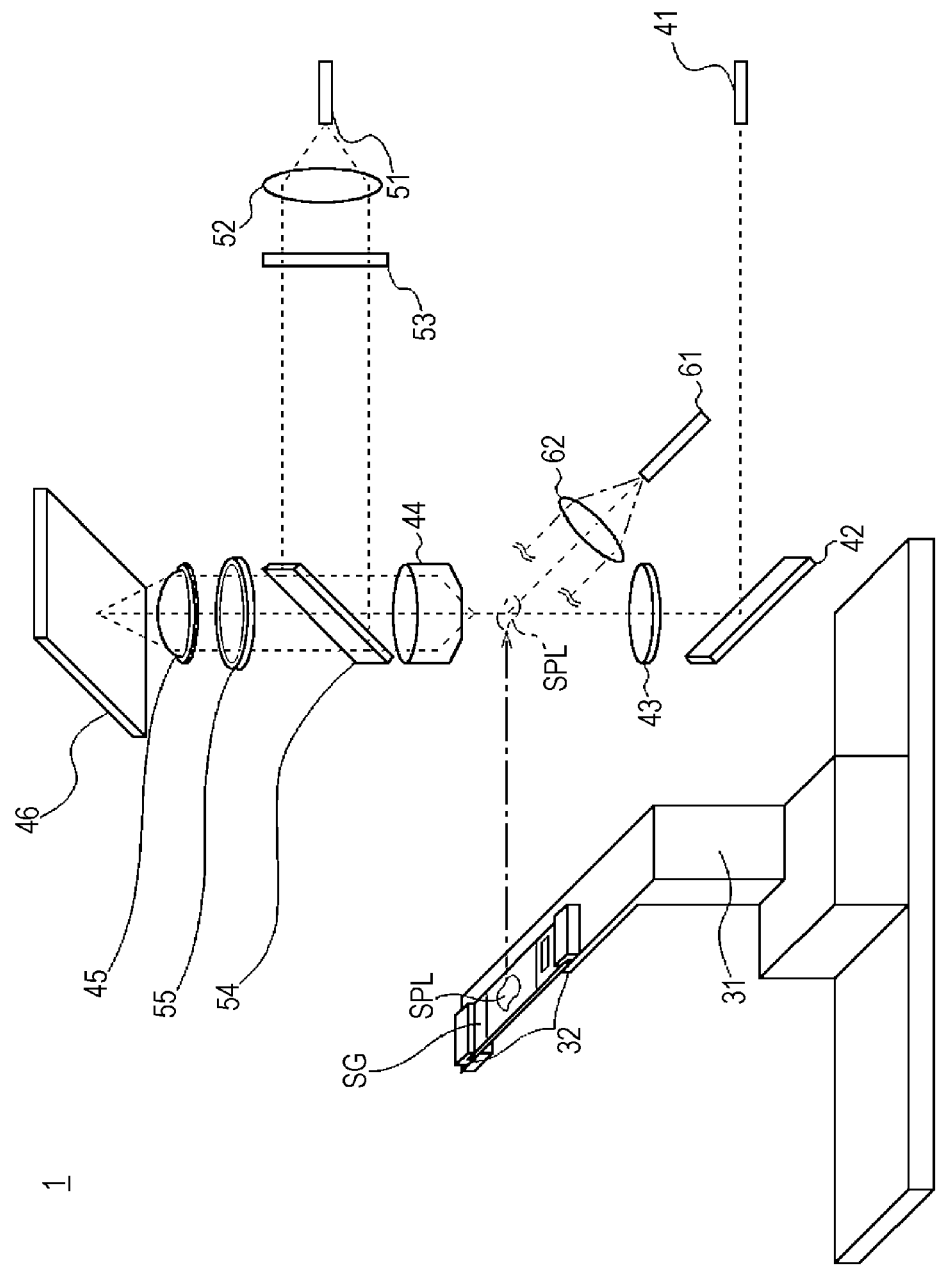
FIG. 13 schematically illustrates another arrangement of the control-marker excitation light source according to still another embodiment.

FIG. 13 illustrates another example with the same reference numerals and symbols applied to the constituents corresponding to those in FIG. 1. In the example shown in FIG. 13, the control-marker excitation light source 61 and the collimator lens 62 are arranged so that the control-marker exclusive excitation light directly falls on the sample surface on the opposite side of the sample surface facing the objective lens 44 at a slant. Like the example shown in FIG. 12, the dichroic mirror 63 shown in FIG. 1 is also omitted in the example shown in FIG. 13. Furthermore, the example shown in FIG. 13 is advantageous because the biological sample SPL can be directly irradiated with the control-marker exclusive excitation light without moving any filter or lens as in the example shown in FIG. 12.

In the embodiments described above, a part of the dark field partial image of the control marker (FIG. 8) is used as the focusing object corresponding to the sample part. While the part is fixed to each sample part allocated with the imaging area AR, it may be variable.

In general, in the biological sample SPL (especially in a tissue section), cells are not evenly present but there are regions where the cells are concentrated and regions where the cells are sparse. In the concentrated region, the fluorescence marker that is truly targeted is more likely to exist compared with the sparse region, and the light intensity of the dark field partial image of the control marker corresponding to the concentrated region is also higher. That is, the concentrated region of the dark field partial image of the control marker is a notable region (a region to be used for focusing).

When the dark field partial image of the control marker corresponding to the sample part to be obtained is read from the imaging device 46 for the first time, all the dark field partial images are read out, and a part of the read dark field partial images is determined to be used for focusing.

This determination technique determines a predetermined number of the parts to be used for focusing in the descending order of the density in a search area smaller than the dark field partial image such as 16×16 pixels or 8×8 pixels. The density can be scaled by, for example, the number of pixels exhibiting the intensity no lower than a threshold in the search area, or the kurtosis (linearity) of intensity histogram of the search area.

While the intensity histogram indicates the distribution of the intensity values in the search area based on the pixels, it is preferable to normalize the distribution assuming the variance indicative of the expanse of the distribution as one. This is because the dark field partial images of sample parts allocated with the imaging areas AR can be scaled in the same units.

In this manner, in each sample part allocated with the imaging area AR, a part in which the fluorescence marker is very likely to exist can be focused on.

In the embodiments described above, the DAPI, which employs the cell nucleus for contrast, is used as the control marker. However, the control marker is not limited to the DAPI. For example, a control marker that targets a cell tissue (or a molecule unique to the cell tissue) may be used, or a control marker that targets a cell cytoplasm (or a molecule unique to the cell cytoplasm) may be used. Naturally, another control marker that targets something else may be used.

Although one type of the control marker is used in the embodiments described above, two or more types of the control marker may be used. In such a case, an exclusive excitation light source is provided with respect to each control marker, or a single excitation light source that excites each control marker but does not excite the fluorescent material in the target is provided, thereby the same effect as in the embodiments described above can be obtained.

In the embodiments described above, a gene is used as the target in the biological sample SPL. However, the target in the biological sample SPL is not limited to the gene. For example, various molecules including a protein molecule such as a cell membrane channel, a glycoprotein molecule, and a sugar chain molecule can be used as the target.

To adjust the focus in the embodiments described above, the movable stage 31 is moved in the z-axis direction (optical axis direction) in the direction of the optical axis of the objective lens 44 that is fixed. Alternatively, the movable stage 31 may be fixed and the objective lens 44 may be moved in the z-axis direction (optical axis direction) against the movable stage 31.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A method of producing an image associated with a biological sample, the method comprising:
    focusing on a portion of the biological sample based on fluorescence of a first fluorescent material, wherein the biological sample is stained with the first fluorescent material and a second fluorescent material;
    activating a light that excites both the first and second fluorescent materials; and
    capturing the image of the portion of the biological sample based on fluorescence of the first fluorescent material and the second fluorescent material, wherein the first and second fluorescent materials have different excitation wavelengths.

2. The method of producing an image associated with a biological sample according to claim 1 wherein the image is produced in a dark field imaging mode.

3. The method of producing an image associated with a biological sample according to claim 1 wherein the image is produced in a dark field imaging mode in combination with a bright field imaging mode.

4. The method of producing an image associated with a biological sample according to claim 1 wherein the image is captured as an entire image.

5. The method of producing an image associated with a biological sample according to claim 1 wherein the image is captured as a partial image.

6. The method of producing an image associated with a biological sample according to claim 1 further comprising combining with the image of the portion of the biological sample images from other portions of the biological sample to compose a whole image of the biological sample.

7. The method of producing an image associated with a biological sample according to claim 1 wherein image production is controlled by a data processing unit including control of focusing and capturing.

8. The method of producing an image associated with a biological sample according to claim 7 wherein after focusing, an excitation light source is driven by the data processing unit to initiate image capturing.

9. The method of producing an image associated with a biological sample according to claim 1 wherein a part of the biological sample is focused at a predetermined location.

10. The method of producing an image associated with a biological sample according to claim 1 wherein a part of the biological sample is focused at a variable location.

11. An apparatus for producing an image associated with a biological sample, the apparatus comprising:
    a base unit configured to receive the biological sample that is stained with a first fluorescent material and a second fluorescent material having different excitation wavelengths;
    a first light source configured to irradiate a portion of the biological sample causing fluorescence of the first fluorescent material; and
    a second light source configured to irradiate the portion of the biological sample to excite both the first and second fluorescent materials causing fluorescence of the first fluorescent material and the second fluorescent material.

12. The apparatus for producing an image associated with a biological sample according to claim 11 wherein the image is produced in a dark field imaging mode.

13. The apparatus for producing an image associated with a biological sample according to claim 11 wherein the image is produced in a dark field imaging mode in combination with a bright field imaging mode.

14. The apparatus for producing an image associated with a biological sample according to claim 11 wherein the image is captured as an entire image.

15. The apparatus for producing an image associated with a biological sample according to claim 11 wherein the image is captured as a partial image.

16. The apparatus for producing an image associated with a biological sample according to claim 11 wherein the image is captured as a plurality of partial images that are connected to form the image.

17. The apparatus for producing an image associated with a biological sample according to claim 11 wherein the apparatus further includes a data processing unit configured to control image production including in communication with the base unit, the first light source and the second light source.

18. The apparatus for producing an image associated with a biological sample according to claim 17 wherein the data processing unit stops driving the first light source and starts driving the second light source to initiate image capturing.

19. The apparatus for producing an image associated with a biological sample according to claim 11 wherein a part of the biological sample is focused at a predetermined location.

20. An apparatus for producing an image associated with a biological sample according to claim 11 wherein a part of the biological sample is focused at a variable location.

21. A computer readable memory device storing instructions to cause a data processing unit to:
- focus on a portion of a biological sample based on fluorescence of a first fluorescent material, wherein the biological sample is stained with the first fluorescent material and a second fluorescent material;
- activate a light that excites both the first and second fluorescent materials; and
- capture an image associated with the portion of the biological sample based on fluorescence of the first fluorescent material and the second fluorescent material, wherein the first and second fluorescent materials have different excitation wavelengths.

22. The computer readable memory device storing instructions to cause a data processing unit, according to claim 21 wherein the image is produced in a dark field imaging mode.

23. The computer readable memory device storing instructions to cause a data processing unit according to claim 21 wherein the image is produced in a dark field imaging mode in combination with a bright field imaging mode.

24. The computer readable memory device storing instructions to cause a data processing unit according to claim 21 wherein the image is captured as an entire image.

25. The computer readable memory device storing instructions to cause a data processing unit according to claim 21 wherein the image is captured as a partial image.

26. The computer readable memory device storing instructions to cause a data processing unit according to claim 21 wherein the image is captured as a plurality of partial images that are connected to form the image.

27. The computer readable memory device storing instructions to cause a data processing unit according to claim 21 wherein after focusing, an excitation light source is driven by the data processing unit to initiate image capturing.

28. The computer readable memory device storing instructions to cause a data processing unit according to claim 21 wherein a part of the biological sample is focused at a predetermined location.

29. The computer readable memory device storing instructions to cause a data processing unit according to claim 21 wherein a part of the biological sample is focused at a variable location.

30. A method of producing an image associated with a biological sample, the method comprising:
- irradiating the biological sample at a first excitation wavelength causing fluorescence of a first fluorescent material within the biological sample;
- focusing on a portion of the biological sample;
- irradiating the biological sample at a second excitation wavelength causing fluorescence of the first fluorescent material and a second fluorescent material with a different excitation wavelength; and
- capturing the image associated with the portion of the biological sample.

31. An apparatus for producing an image associated with a biological sample, the apparatus comprising:
- a first light source configured to irradiate a portion of the biological sample at a first excitation wavelength causing fluorescence of a first fluorescent material within the biological sample; and
- a second light source configured to irradiate the biological sample at a second excitation wavelength to excite the first fluorescent material and a second fluorescent material with a different excitation wavelength.

* * * * *